United States Patent [19]

Maryanoff

[11] Patent Number: 4,713,386
[45] Date of Patent: Dec. 15, 1987

[54] TETRAHYDROAZETO [2,1-A]ISOQUINOLINES AND METHODS FOR TREATING DEPRESSION

[75] Inventor: Bruce E. Maryanoff, New Hope, Pa.

[73] Assignee: McNeilab, Inc., Fort Washington, Pa.

[21] Appl. No.: 909,793

[22] Filed: Sep. 22, 1986

[51] Int. Cl.$^4$ .................. A61K 31/435; C07D 471/04
[52] U.S. Cl. ..................................... 514/294; 546/94; 546/144; 540/205
[58] Field of Search .......................... 546/94; 514/294

[56] References Cited

U.S. PATENT DOCUMENTS 4,595,688  6/1986  Maryanoff ........................... 514/285
4,622,327  11/1986  Bernath et al. ..................... 514/294

OTHER PUBLICATIONS

"Pyrroloisoquinoline Antidepressants, Potent, Enantioselective Inhibition . . . ", J. of Med. Chem., 1984, 27, No. 8, Maryanoff et al., pp. 943-946.
"Resolution and Absolute Configuration of 1,2,3,5,6,10bβ-Hexahydro-6α-phenylpyrrolo[2,1-α] . . . ", Maryanoff et al., J. Heterocyclic Chem., 22, pp. 911-914, (1985).
"Stereochemical Studies, 100[1], Saturated Meterocycles, 104[1] Synthesis, And NMR and X-Ray Study of 1-Substituted . . . ", Hetrahedron, vol. 42, No. 18, pp. 5139-5148, Bernath et al., (1986).
"Synthesis and Stereochemistry of 7-Phenyl-2-propionanilidobenzo[a]quinolizidine Derivatives . . . ", Maryanoff et al., J. of Med. Chem., vol. 24, No. 1, pp. 79-88, (1981).

Primary Examiner—Henry R. Jiles
Assistant Examiner—J. Richter
Attorney, Agent, or Firm—David J. Levy

[57] ABSTRACT

Tetrahydroazeto[2,1-a]isoquinoline of the formula (I):

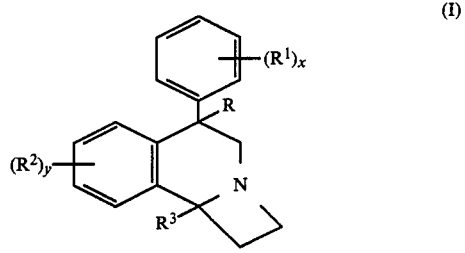

wherein R, $R^1$, $R^2$ and $R^3$ are substituents and x and y are 0-2. Also pharmaceutical compositions for relieving depression in mammals, e.g. in humans, and methods for synthesis and use of formula (I) compounds as well as novel intermediates in the synthesis.

16 Claims, No Drawings

TETRAHYDROAZETO [2,1-A]ISOQUINOLINES AND METHODS FOR TREATING DEPRESSION

The present invention comprises certain tetrahydroazetoisoquinoline compounds including acid addition salts thereof, methods for their preparation and use, pharmaceutical compositions and intermediates used in their synthesis. Pyrroloisoquinoline antidepressant compounds are disclosed by Bruce E. Maryanoff et al. on page 943 of J. Med. Chem. Vol. 27 (1984), in J. Heterocyclic Chem. Vol 22, page 911 (1985) and in U.S. Pat. No. 4,595,688. G. Bernath et al. discloses 2H-azeto[2,1-a]isoquinoline derivatives in DE No. 3,439,157 which is also shown in Chem. Abstracts 103: 160406k.

SUMMARY OF THE INVENTION

Compounds of the present invention are of the following formula (I):

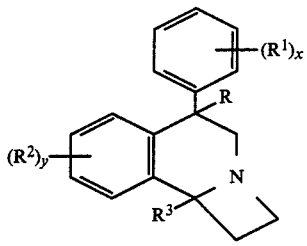

and acid addition salts wherein R, $R^1$, $R^2$ and $R^3$ are substituents and x and y are the integers 0–2. Also included within the invention are pharmaceutical compositions, methods for the synthesis of formula (I) compounds and intermediates used in such synthesis.

DETAILED DESCRIPTION OF THE INVENTION

Compounds of the present invention are 1,4,5,9b-tetrahydroazeto[2,1-a]isoquinolines of the following formula (I):

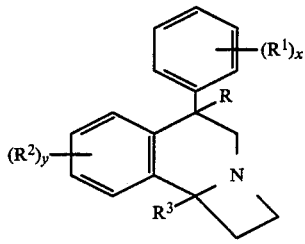

wherein
R is hydrogen or alkyl;
$R^1$ is independently halogen, alkyl, alkoxy, alkylthio, perfluoroalkyl or nitro;
$R^2$ is independently halogen, alkyl or alkoxy;
$R^3$ is hydrogen or alkyl;
x is the integer 0, 1 or 2; and
y is the integer 0, 1 or 2;
and the pharmaceutically-acceptable acid-addition salts thereof.

Pharmaceutical compositions of the invention comprise the formula (I) compounds as defined above in combination with pharmaceutically-acceptable carriers or diluents.

R, in more detail, is hydrogen or alkyl of about 1 to 4 carbons such as methyl, ethyl, n-propyl, 2-propyl, n-butyl, sec-butyl and tert-butyl.

$R^1$, in more detail, is independently, e.g. two different $R^1$ moieties may be attached to the phenyl ring when x is 2, halogen such as fluoro, chloro, bromo or iodo; alkyl of about 1 to 4 carbons such as methyl, ethyl, n-propyl, 2-propyl, n-butyl, sec-butyl and tert-butyl; alkoxy of about 1 to 4 carbons such as methoxy, ethoxy, isopropoxy and tert-butoxy; alkylthio of about 1 to 4 carbons such as methylthio or ethylthio; perfluoroalkyl of about 1 to 4 carbons such as trifluoromethyl.

$R^2$, in more detail, is independently, e.g. two of the same or different $R^2$ moieties may be attached to the phenyl ring when y is 2, halogen such as fluoro, chloro, bromo or iodo; alkyl of about 1 to 4 carbons such as methyl, ethyl, n-propyl, 2-propyl, n-butyl, sec-butyl and tert-butyl; or alkoxy of about 1 to 4 carbons such as methoxy, ethoxy, isopropoxy and tert-butoxy.

$R^3$, in more detail, is hydrogen or alkyl of about 1 to 4 carbons such as methyl or ethyl.

Particular compounds of formula (I) include those where R is hydrogen and where x and y are both 0. Included within this group are the following:
cis-1,4,5,9b-tetrahydro-5-phenyl-2H-azeto[2,1-a]isoquinoline; and
trans-1,4,5,9b-tetrahydro-5-phenyl-2H-azeto[2,1-a]isoquinoline
and the pharmaceutically-acceptable acid-addition salts thereof.

Various isomers are possible in formula (I) compounds and the present invention includes all such individual enantiomers, diastereomers, racemates and other isomer ratios. Resolution of enantiomers shown in the application, of course, results in single enantiomer without its enantiomeric mirror image. The isomers, isolated in their pure form, may differ in biological activity. The compounds of formula (I) constitute valuable therapeutic agents by their possession of psychotropic activity, particularly antidepressant activity.

The various diastereomers of each formula (I) compound are distinguished herein using the nomenclature recommended by Chemical Abstracts for representing the relative configuration of diastereomers of fused-ring compounds having two stereocenters (cis/trans nomenclature). This requires that the stereochemical position of a substituent attached to a first stereocenter relative to a substituent attached to a second stereocenter be either in the same plane (i.e., cis) or in opposite planes (i.e., trans) to each other. Particular compounds of formula (I) are those where the $(R^1)_x$ substituted phenyl ring in the 5-position and the 9b-position hydrogen atom are cis or trans to each other. For example compounds of the following formulae (Ic) and (It):

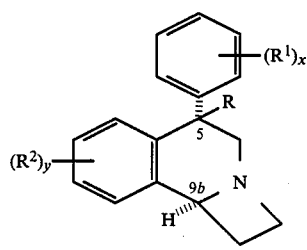

-continued

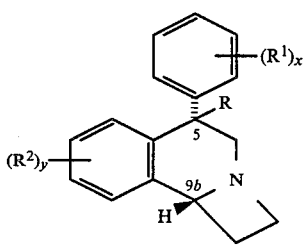
(It)

Representative salts of the compounds of formula (I) which may be used include those made with acids such as hydrochloric, hydrobromic, hydroiodic, perchloric, sulfuric, nitric, phosphoric, acetic, propionic, glycolic, lactic, pyruvic, malonic, succinic, maleic, fumaric, malic, tartaric, citric, benzoic, cinnamic, mandelic, methanesulfonic, ethanesulfonic, hydroxyethanesulfonic, benzenesulfonic, p-toluenesulfonic, cyclohexanesulfamic, salicylic, p-aminosalicylic, 2-phenoxybenzoic, 2-acetoxybenzoic or a salt made with saccharin. Such salts can be made by reacting the free base of (I) with the acid and recovering the salt.

The compounds of this invention may be prepared by the following Reaction Schemes 1 and 2:

Reaction Scheme 1:

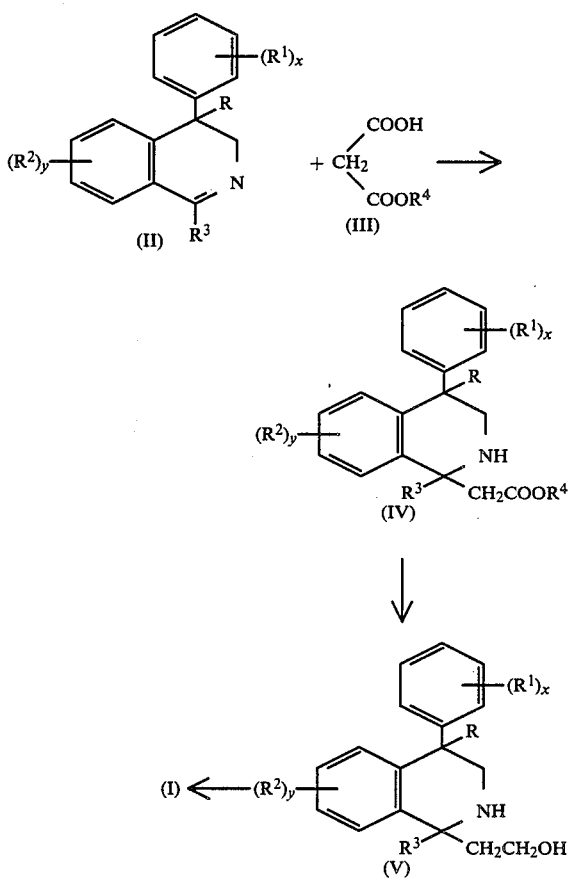

In Reaction Scheme 1, an appropriately substituted 3,4-dihydro-4-phenylisoquinoline of formula (II) where R, $R^1$, $R^2$, $R^3$, x and y are as defined in formula (I) may be prepared by the method described by Maryanoff et al. in J. Med. Chem. Vol 24, page 79 (1981) or related methods. A monoalkyl malonate of formula (III), wherein $R^4$ is alkyl of about 1 to 4 carbons such as methyl or ethyl may be prepared by the method of R. E. Strube, Org. Syn. Vol. IV, page 417. The isoquinoline (II) and the malonate (III) may be reacted at a temperature of about 100° C. to 120° C. in the absence of a solvent for a period of about 15 minutes to about two hours to produce a tetrahydroisoquinoline acetic ester of formula (IV), by the method described by M. Cava et al. in Vol. 26 of Tetrahedron Lett., page 1259 (1985). The ester is then reduced to the corresponding amino alcohol of formula (V), substituents being as defined for formula (I), by the action of a hydride reducing agent such as lithium aluminum hydride, LiAlH(OMe)$_3$ or AlH$_3$ in an ether-like solvent such as tetrahydrofuran or diethyl ether of mixtures thereof. The reaction is generally carried out at a temperature of about 0° C. to about 35° C. Reaction times of about 15 min to about 2 hr are generally sufficient for complete reduction. The amino alcohol of formula (V) may be purified by methods known to those skilled in the art of organic chemistry, e.g. chromatography or crystallization. The amino alcohol of formula (V) is then converted to its corresponding acid-addition salt by the addition of a mineral acid such as hydrogen bromide and the acid-addition salt is cyclized to the corresponding 1,4,5,9b-tetrahydroazeto[2,1-a]isoquinoline of formula (I) by treatment with diethyl azodicarboxylate and triphenylphosphine in an inert solvent such as benzene, toluene or N,N-dimethylformamide. The reaction takes place over a period of about 4 hours to about 24 hours at a temperature of about 60° C. to about 100° C. with about 25° C. being preferred. The resultant product of formula (I) is usually a mixture of diastereomers which may be separated by methods known in the art of organic chemistry such as liquid chromatography or fractional crystallization of free bases, or by fractional crystallization of acid-addition salts.

An alternate route to prepare compounds of formula (I) involves the conversion of an ester of formula (IV) to the corresponding acid of formula (VI), cyclization of the acid to an azetidine-2-one of formula (VII) and reduction of the azetidine-2-one to the corresponding azetidine of formula (I) as shown in the following Reaction Scheme 2.

Reaction Scheme 2:

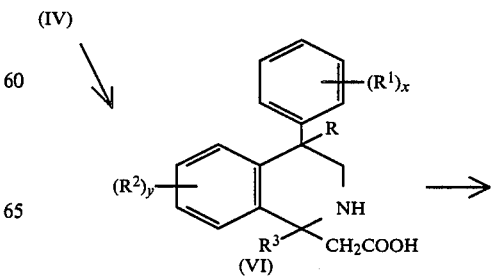

-continued
Reaction Scheme 2:

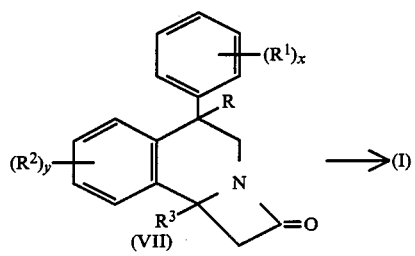
(VII) → (I)

In more detail, in Reaction Scheme 2 an ester of formula (IV) is first converted to the corresponding acid of formula (VI) by standard hydrolytic conditions such as heating (IV) in aqueous acid or base at a temperature of about 50° C. to about 100° C. for a period of about 30 minutes to about 30 hr and obtaining the product acid of formula (VI) by standard extraction techniques. The acid of formula (VI) is then cyclized to form an azetidine-2-one of formula (VII) by dehydration using various techniques such as those described in a publication by A. K. Mukerjee et al. on pages 1731–1767, Vol. 34 of Tetrahedron (1978). The azetidine-2-one of formula (VII) is then reduced to the corresponding azetidine of formula (I) by the action of hydride reducing agents, particularly diisobutyl aluminum hydride and $AlH_2Cl$, as described by I. Ojima et al. in Vol. 105 of J. Am. Chem. Soc., page 6339 (1983) and Tetrahedron Lett., Vol. 26, page 2035 (1985) in an inert solvent such as ether, THF, toluene or hexane at temperatures from about 25° C. to near the boiling point of the solvent for a period of about 30 min to 6 hr.

The diastereomers of formula (I) compounds may be interconverted by base-induced exchange of protons at the 5- and/or 9b-positions. Specifically, heating of amine diastereomers of formula (I) possessing 5 and/or 9b protons in aqueous dimethyl sulfoxide around 80°–150° C. in the presence of an alkali metal hydroxide such as sodium hydroxide for about 1 to 60 hr can give rise to equilibrium mixtures of diastereomers. Such equilibrium tactics can enhance the proportions of minor diastereomers in comparison to the original product mixtures from cyclization. Also, a less active isomer may be interconverted to a more active isomer by this method.

In addition to the novel compounds of formula (I) of this invention, certain other compounds of this invention are novel and useful as intermediates in the preparation of formula (I) compounds. For example, compounds of formulae (IV), (V), (VI) and (VII) wherein R, $R^1$, $R^2$, $R^3$, $R^4$, x and y are as defined above, are considered within the definition of the present invention. Acid-addition salts of compounds of formulae (IV), (V) and (VI) and alkali metal addition salts of compounds of formula (VI) are included within this definition. In addition to their utility as intermediates, compounds of formulae (IV), (V), (VI) and (VII) may possess useful pharmacological activity of their own such as antidepressant or antibiotic activity.

The useful central nervous system activity of the compounds of formula (I) of the invention, more particularly antidepressant activity, may be demonstrated by a standard test for antidepressant agents known as the Tetrabenazine Antagonism Assay which is described in U.S. Pat. No. 3,787,577. In this test, mice are injected with a test compound 30 min prior to the injection of 32 mg/kg i.p. of TBZ, a drug which decreases normal exploratory activity and induces ptosis. After 30 min. the mice are tested for two parameters: the presence of normal exploratory activity (EA) and reversal of ptosis (Pt). A control group of mice is given only 32 mg/kg i.p. of TBZ. The biological activity of the novel compounds of this invention may be understood by the representative, nonlimiting example, presented in Table I.

The Tetrabenazine Antagonism Assay results for one compound of formula (I) of the present invention are shown in Table I.

TABLE I

| Compound of Example No. | Structure[a] | % inhibition @ 3 mg/kg EA/Pt (i.p.) | $ED_{50}$[b] ptosis (i.p.) |
|---|---|---|---|
| 1d |  | 50%/88% | 1.25 |

[a]Structure of free base is shown (x = 0, y = 0, R = H).
Compound tested was the (1:1) fumarate salt.
[b]$ED_{50}$ in mg/kg.

Based on the above results, compounds of the invention may be used to treat depression in warm-blooded animals such as humans by administration of an antidepressant effective dose. The dosage range would be from about 10 to 2000 mg, in particular about 200 to 500 mg of active ingredient 1 to 4 times per day for an average (70 kg) human although it is apparent that activity of individual compounds of the invention will vary as will the depression being treated.

To prepare the pharmaceutical compositions of this invention, one or more compounds or salts thereof of the invention as the active ingredient, is intimately admixed with a pharmaceutical carrier according to conventional pharmaceutical compounding techniques, which carrier may take a wide variety of forms depending on the form of preparation desired for administration, e.g. oral or parenteral such as intramuscular. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, th carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, from about 2.5 mg to about 2000 mg of the active ingredient.

In the following Examples and throughout the specification, the following abbreviations may be used: mg (milligrams); g (grams); ml (milliliters); N (normal); mp (melting point); E (trans); Z (cis); Et$_2$O (diethylether); EtOAc (ethyl acetate); MeOH (methanol); EtOH (ethanol); LAH (lithium aluminum hydride); DMF (dimethylformamide); p.o. (per os, orally); i.p. (intraperitoneal); HPLC (high pressure liquid chromatography); hr (hours); min (minutes); and C, H, N, O etc. (the chemical symbols for the elements). Unless otherwise indicated, all temperatures are reported in °C. (degrees centigrade) and all references to ether are to Et$_2$O.

EXAMPLE 1

1,4,5,9b-Tetrahydro-5-phenyl-2H-azeto[2,1-a]isoquinoline-(E)-2-butenedioate a.

Ethyl 1,2,3,4-tetrahydro-4-phenyl-1-isoquinolineacetate

A mixture of 8.6 g (0.06 mole) of monoethyl malonate and 10.0 g (0.048 mole) of 3,4-dihydro-4-phenylisoquinoline was stirred in a preheated oil bath at 120° C. for 45 min to give 14.0 g (98.7%) of ethyl 1,2,3,4-tetrahydro-4-phenyl-1-isoquinolineacetate as a pale yellow syrup. The ester was used in the next step without further purification.

b.

1,2,3,4-Tetrahydro-4-phenyl-1-isoquinolineethanol

A mixture of the ester obtained in Example 1a, 90 ml of diethyl ether and 1 ml of tetrahydrofuran was added dropwise to a slurry of 5.4 g (0.14 mole) of LAH in 140 ml of Et$_2$O while stirring under an atmosphere of nitrogen. Stirring was continued for 45 min followed by cautious addition of 5.4 ml of water, 10.8 ml of 15% sodium hydroxide solution and 10.8 ml of water. After stirring vigorously for 30 min, the solids were removed by filtration and the filtrate was washed with 3N sodium hydroxide solution. The organic phase was separated and dried over anhydrous magnesium sulfate and the solvents removed in vacuo to yield the crude title compound as a syrup. The syrup was purified by HPLC on a Waters Prep 500 chromatograph using a silica column and elution with EtOAc/hexane/MeOH, 4:1:0.5, to give 7.2 g (60%) of the free base of the title amino alcohol as a syrup which crystallized slowly. Proton magnetic resonance revealed the product to be a 2:1 trans/cis mixture of diastereomers. The amino alcohol was converted to the corresponding hydrobromide salt in acetone solution by treatment of the free base with anhydrous hydrogen bromide. The solvent was removed in vacuo to yield the title compound as a light brown solid. The solid was used in the next step without further purification.

c.

cis-1,4,5,9b-Tetrahydro-5-phenyl-2H-azeto[2,1-a]isoquinoline (E)-2-butenedioate

A mixture of 2.24 g (0.008 mole) of triphenylphosphine and 2.8 g (0.008 mole) of the amino alcohol hydrobromide from Example 1b in 30 ml of benzene and 60 ml of DMF was treated dropwise with 1.4 g (0.008 mole) of diethyl azodicarboxylate. The reaction mixture was stirred under an atmosphere of argon for 3.5 hr and the solvents removed under vacuum. The resulting syrup was treated with 3N sodium hydroxide solution and extracted into diethyl ether. The organic extract was washed with brine, dried over anhydrous magnesium sulfate and concentrated in vacuo to give a syrup. The syrup was purified by HPLC on a Waters Prep 500 chromatograph using a silica column and eluting with EtOAc/MeOH (2:1). The first compound-bearing fractions were combined and concentrated in vacuo to yield 0.22 g of the free base of the cis diastereomer of the title compound, a light yellow solid. The title compound was obtained by treatment of a solution of the free base in 2-propanol with one equivalent of fumaric acid. Recrystallization from 2-propanol yielded the title compound, an off-white solid, mp 145°–146° C.

d.

trans-1,4,5,9b-Tetrahydro-5-phenyl-2H-azeto[2,1-a]isoquinoline (E)-2-butenedioate The second compound-bearing fractions from the chromatography of Example 1c containing the trans diastereomer were combined and concentrated in vacuo to yield 0.3 g of the free base of the trans diastereomer as a syrup. The free base was converted to the corresponding fumarate by treatment with one equivalent of fumaric acid as described in Example 1c to yield the title compound as an off-white solid, mp 163°–164° C.

What is claimed is:

1. A 1,4,5,9b-tetrahydroazeto[2,1-a]isoquinoline of the following formula (I):

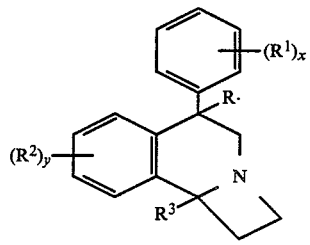

wherein
R is hydrogen or alkyl;
R$^1$ is independently halogen, alkyl, alkoxy, alkylthio, perfluoroalkyl or nitro;
R$^2$ is independently halogen, alkyl or alkoxy;
R$^3$ is hydrogen or alkyl;
x is the integer 0, 1 or 2; and
y is the integer 0, 1 or 2;
wherein said alkyl for R, R$^1$, R$^2$ and R$^3$ is alkyl of about 1 to 4 carbons, said alkoxy for R$^1$ and R$^2$ is alkoxy of about 1 to 4 carbons, said alkylthio for R$^1$ is alkylthio of about 1 to 4 carbons and said perfluoroalkyl for R$^1$ is perfluoroalkyl of about 1 to 4 carbons,
and the pharmaceutically-acceptable acid-addition salts thereof.

2. The 1,4,5,9b-tetrahydroazeto[2,1-a]isoquinoline of claim 1, wherein said halogen for R$^1$ and R$^2$ is fluoro, chloro, bromo, or iodo.

3. The 1,4,5,9b-tetrahydroazeto[2,1-a]isoquinoline of claim 1, wherein R is hydrogen.

4. The 1,4,5,9b-tetrahydroazeto[2,1-a]isoquinoline of claim 1, wherein x is the integer 0.

5. The 1,4,5,9b-tetrahydroazeto[2,1-a]isoquinoline of claim 1, wherein y is the integer 0.

6. The 1,4,5,9b-tetrahydroazeto[2,1-a]isoquinoline of claim 1, wherein both x and y are the integer 0.

7. The 1,4,5,9b-tetrahydroazeto[2,1-a]isoquinoline of claim 1, wherein both x and y are the integer 0 and R is hydrogen.

8. The 1,4,5,9b-tetrahydroazeto[2,1-a]isoquinoline of claim 1, wherein the $(R^1)_x$ substituted phenyl ring in the 5-position and the 9b-position hydrogen atom are cis to each other.

9. The 1,4,5,9b-tetrahydroazeto[2,1-a]isoquinoline of claim 1, wherein the $(R^1)_x$ substituted phenyl ring in the 5-position and the 9b-position hydrogen atom are trans to each other.

10. The 1,4,5,9b-tetrahydroazeto[2,1-a]isoquinoline of claim 1, wherein said 1,4,5,9b-tetrahydroazeto[2,1-a]isoquinoline of formula (I) is selected from the group consisting of:
cis-1,4,5,9b-tetrahydro-5-phenyl-2H-azeto[2,1-a]isoquinoline; and
trans-1,4,5,9b-tetrahydro-5-phenyl-2H-azeto[2,1-a]isoquinoline.

11. The 1,4,5,9b-tetrahydroazeto[2,1-a]isoquinoline of claim 1, wherein said 1,4,5,9b-tetrahydroazeto[2,1-a]isoquinoline is cis-1,4,5,9b-tetrahydro-5-phenyl-2H-azeto[2,1-a]isoquinoline.

12. The 1,4,5,9b-tetrahydroazeto[2,1-a]isoquinoline of claim 1, wherein said 1,4,5,9b-tetrahydroazeto[2,1-a]isoquinoline is trans-1,4,5,9b-tetrahydro-5-phenyl-2H-azeto[2,1-a]isoquinoline.

13. A pharmaceutical composition for the treatment of depression which comprises a pharmaceutically-acceptable carrier or diluent and an amount sufficient to alleviate the symptoms of depression of 1,4,5,9b-tetrahydroazeto[2,1-a]isoquinoline of claim 1.

14. The pharmaceutical composition of claim 13, wherein said halogen for $R^1$ and $R^2$ is fluoro, chloro, bromo or iodo.

15. The pharmaceutical composition of claim 13, wherein said 1,4,5,9b-tetrahydroazeto[2,1-a]isoquinoline is trans-1,4,5,9b-tetrahydro-5-phenyl-2H-azeto[2,1-a]isoquinoline.

16. A method of relieving depression in a mammal which comprises administering to the mammal a pharmaceutical composition of claim 13.

* * * * *